United States Patent [19]

Naeumann et al.

[11] Patent Number: 5,008,461
[45] Date of Patent: Apr. 16, 1991

[54] PREPARATION OF BENZYL KETONES

[75] Inventors: Fritz Naeumann, Mannheim; Eckhard Hickmann, Dannstadt-Schauernheim, both of Fed. Rep. of Germany

[73] Assignee: BASF Aktiengesellschaft, Ludwigshafen, Fed. Rep. of Germany

[21] Appl. No.: 489,690

[22] Filed: Mar. 7, 1990

[30] Foreign Application Priority Data

Mar. 30, 1989 [DE] Fed. Rep. of Germany ....... 3910220

[51] Int. Cl.$^5$ .............................................. C07C 45/52
[52] U.S. Cl. ...................................................... 568/322
[58] Field of Search ......................................... 568/322

[56] References Cited

U.S. PATENT DOCUMENTS 3,491,153 1/1970 Lyness ................................. 568/322
3,920,668 11/1975 Nickl et al. ......................... 568/322
4,230,893 10/1980 Gal ..................................... 568/322

FOREIGN PATENT DOCUMENTS 870658 5/1971 Canada ............................... 568/322

OTHER PUBLICATIONS

Chem. Abstr., vol. 105, 190 622z.

Primary Examiner—James H. Reamer
Attorney, Agent, or Firm—John H. Shurtleff

[57] ABSTRACT

Benzyl ketones of the general formula I

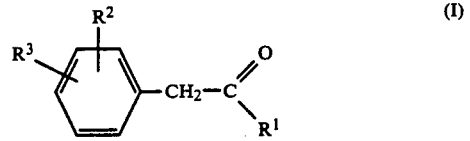

where $R^1$ is $C_1$-$C_8$-alkyl which is unsubstituted or substituted by cycloalkyl or aryl and $R^2$ and $R^3$ are each halogen, $C_1$-$C_4$-alkyl, hydroxyl, $C_1$-$C_4$-alkoxy or $C_2$-$C_4$-methylenedioxy, are prepared by a process in which a glycol monoether of the general formula II

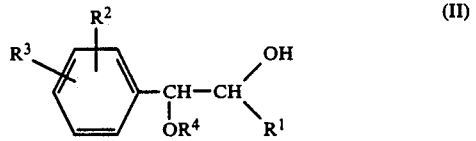

where $R^1$, $R^2$ and $R^3$ have the abovementioned meanings and $R^4$ is $C_1$-$C_8$-alkyl, is converted in the presence of silica, a phosphate or a zeolite at from 50° to 500° C. and under from 0.01 to 50 bar.

6 Claims, No Drawings

PREPARATION OF BENZYL KETONES

The present invention relates to a novel and improved process for the preparation of benzyl ketones by bringing glycol monoethers into contact with phosphates, silica or zeolites.

Houben-Weyl, Methoden der Organischen Chemie, volume VII/2a, pages 931, 932, 968 and 981, discloses the preparation of benzyl ketones by subjecting aryl-substituted oxiranes or glycols to a rearrangement reaction over homogeneous catalysts, such as cold concentrated or hot dilute sulfuric acid, glacial acetic acid, phosphoric acid, hydrochloric acid and acetyl chloride, or heterogeneous catalysts, such as $SiO_2$, aluminum silicates or zeolites. It is known that phenylated ethylene glycols can, for example, be dehydrated, over amorphous aluminum silicates doped with $Fe_2O_3$, CaO and MgO (Chem. Abstr. Vol. 82, 170 375) or clay (Chem. Abstr. Vol. 81, 120 220), in suspension under pressure, to give phenylacetaldehydes in yields of from 50 to 86%. U.S. Pat. No. 2,444,400 discloses the dehydration of various phenylethylene glycols by acid catalysis (e.g. kieselguhr, silica or phosphoric acid/carrier). The starting materials used include compounds having a phenyl nucleus substituted by halogen, alkoxy or alkyl. Chem. Abstr. Vol. 105, 190 662 mentions the use of aluminosilicate zeolites of the pentasil type or mordenite. Furthermore, U.S. Pat. No. 2,628,255 discloses that styrene oxides can be subjected to a rearrangement reaction in the gas phase to give phenylacetaldehyde, inter alia over Mg silicate. Chem. Abstr. Vol. 105, 190 662 discloses that styrene oxide can be subjected to a rearrangement reaction over zeolites, including those of the pentasil type, and Chem. Abstr. Vol 81, 120 220 discloses that styrene oxides and styrene glycols can be subjected to a rearrangement reaction with acid catalysis to give aldehydes, using, inter alia, activated clays. However, the disadvantage of these processes is that it is necessary to use either the oxiranes, which have cytotoxic and/or genotoxic properties and therefore necessitate special safety measures, or the glycols, which are prepared from the corresponding oxiranes by hydrolysis and are inconvenient to isolate owing to their good water-solubility and difficult to vaporize because of their high boiling points.

It is an object of the present invention to provide a novel and improved process for the preparation of benzyl ketones and to overcome the disadvantages of the known processes.

We have found that this object is achieved by a novel and improved process for the preparation of benzyl ketones of the general formula I

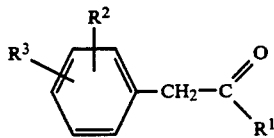
(I)

where $R^1$ is $C_1$–$C_8$-alkyl which is unsubstituted or substituted by cycloalkyl or aryl and $R^2$ and $R^3$ are each halogen, $C_1$–$C_4$-alkyl, hydroxyl, $C_1$–$C_4$-alkoxy or $C_2$–$C_4$-methylenedioxy, wherein a glycol monoether of the general formula II

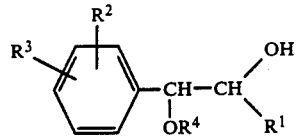
(II)

where $R^1$, $R^2$ and $R^3$ have the abovementioned meanings and $R^4$ is $C_1$–$C_8$-alkyl, is converted in the presence of silica, of phosphate or a zeolite at from 50° to 500° C. and under from 0.01 to 50 bar.

The benzyl ketones I are obtainable by the following method:

The reaction is carried out by heating glycol monoethers II over silica, a phosphate or a zeolite with elimination of $R^4$—OH.

The reaction can be carried out either in the liquid phase or batchwise or, preferably, continuously in the gas phase at from 50° to 500° C. and under from 0.01 to 50 bar.

The liquid phase reaction can be carried out, for example, as a suspension, trickle-bed or bottoms reaction at from 50° to 200° C. and under from 0.5 to 20 bar, preferably at from 70° to 170° C. and under from 1 to 5 bar.

The preferred gas phase reaction can be effected, for example, at from 100° to 500° C., preferably from 150° to 450° C., and under from 0.1 to 50 bar, particularly preferably at from 200° to 400° C. and under from 0.5 to 5 bar. In the reaction in the gas phase, the weight hourly space velocity (WHSV) of from 0.1 to 20, in particular from 0.6 to 5, g of starting material of the formula II per g of catalyst per hour is advantageously maintained. The gas phase reaction can be carried out in a fixed bed or in a fluidized bed.

The process is generally carried out under atmospheric pressure or, depending on the volatility of the starting compound, under reduced or superatmospheric pressure, preferably continuously.

Sparingly volatile or solid starting materials are used in dissolved form, for example in solution in tetrahydrofuran, toluene or petroleum ether. In general, dilution with these solvents or inert gases, such as $N_2$, Ar or $H_2O$ vapor, is also possible.

After the reaction, the resulting products are isolated from the reaction mixture by conventional methods, for example by distillation; unconverted starting materials may be recycled to the reaction. Owing to the high yields, the reaction products can also be further processed directly.

Gaseous reaction products are preferably immediately fed to a separation stage and are separated into their individual components, for example in a fractionation column.

The glycol monoethers II are obtained in a technically simple manner by epoxidation of the corresponding styrenes with $H_2O_2$ under Payne conditions (Organic Synthesis 60 (19...), 63), for example

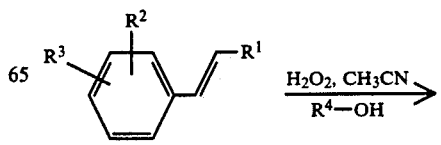

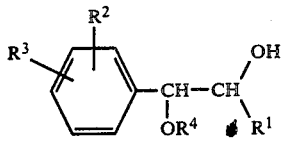

In the compounds of the formulae I and II,

R¹ is straight-chain or branched $C_1$-$C_8$-alkyl, preferably straight-chain or branched $C_1$-$C_4$-alkyl, such as methyl, ethyl, n-propyl, isopropyl, n-butyl, isobutyl, sec-butyl or tert-butyl, preferably methyl or ethyl, R² and R³ independently of one another are substituents in the ortho-, meta- and/or para-position, and are each halogen, such as fluorine, chlorine, bromine or iodine, straight-chain or branched $C_1$-$C_4$-alkyl, such as methyl, ethyl, n-propyl, isopropyl, n-butyl, isobutyl, sec-butyl or tert-butyl, preferably methyl or ethyl, hydroxyl, straight-chain or branched $C_1$-$C_4$-alkoxy, such as methoxy, ethoxy, n-propoxy, isopropoxy, n-butoxy, isobutoxy, sec-butoxy or tert-butoxy, preferably methoxy or ethoxy, or 3-methoxy-4-hydroxy, methylenedioxy, preferably methylenedioxy in the 3,4-position on the phenyl ring, and R⁴ is straight-chain or branched $C_1$-$C_8$-alkyl, preferably straight-chain or branched $C_1$-$C_4$-alkyl, such as methyl, ethyl, n-propyl, isopropyl, n-butyl, isobutyl, sec-butyl or tert-butyl, preferably methyl or ethyl.

The following are preferred glycol monoethers II for the novel process:
1-methoxy-1-phenylpropan-2-ol,
1-methoxy-1-(4-fluorophenyl)-propan-2-ol,
1-methoxy-1-(2-chlorophenyl)-propan-2-ol,
1-methoxy-1-(4-methylphenyl)-propan-2-ol,
1-methoxy-1-(4-methoxyphenyl)-propan-2-ol,
1-methoxy-(3,4-methylenedioxyphenyl)-propan-2-ol,
1-methoxy-(3-methoxy-4-hydroxy)-propan-2-ol.

Accordingly, the following are obtained as preferred products I of the novel process:
1-phenylpropan-2-one,
1-(4-fluorophenyl)-propan-2-one,
1-(2-chlorophenyl)-propan-2-one,
1-(4-methylphenyl)-propan-2-one,
1-(4-methoxyphenyl)-propan-2-one,
1-(3,4-methylenedioxyphenyl)-propan-2-one,
1-(3-methoxy-4-hydroxy)-propan-2-one.

Suitable catalysts for the novel process for the preparation of benzyl ketones are zeolites, in particular acidic zeolites. Zeolites are crystalline aluminosilicates which have a highly ordered structure with a rigid three-dimensional network of $SiO_4$ and $AlO_4$ tetrahedra which are bonded by common oxygen atoms. The ratio of Si and Al atoms to oxygen is 1:2. The electrovalency of the aluminum-containing tetrahedra is balanced by inclusion of cations in the crystal, for example of an alkali metal or hydrogen ion. Cation exchange is possible. The voids between the tetrahedra are occupied by water molecules prior to dehydration by drying or calcining.

In the zeolites, other trivalent and divalent elements, such as B, Ga, Fe, Cr, Be, As or Sb, may be incorporated in the framework instead of aluminum, or the silicon can be replaced by a tetravalent element, such as Ge, Ti, Zr or Hf.

Suitable catalysts are zeolites of the mordenite group or faujasite group, such as L zeolites, or finepored zeolites of the erionite or chabasite type. Zeolites of the pentasil type are particularly advantageous for the novel process. These zeolites may have different chemical compositions. They are aluminosilicate, borosilicate, ferrosilicate, gallium silicate, chromium silicate, beryllium silicate, arsenosilicate, antimony silicate and bismuth silicate zeolites or mixtures thereof, and aluminogermanate, borogermanate, gallium germanate and ferrogermanate zeolites or mixtures thereof.

The aluminosilicate, borosilicate, gallium silicate and ferrosilicate zeolites of the pentasil type are particularly suitable for the novel process. The aluminosilicate zeolite is prepared, for example, from an aluminum compound, preferably $Al(OH)_3$ or $Al_2(SO_4)_3$, and a silicon component, preferably finely divided silica, in aqueous amine solution, in particular in 1,6-hexanediamine or 1,3-propanediamine or triethylenetetramine solution, with or, in particular, without the addition of an alkali or alkaline earth, at from 100° to 220° C. under autogenous pressure. The isotactic zeolites according to DE-A-3 006 471 are also suitable. The aluminosilicate zeolites obtained have an $SiO_2/Al_2O_3$ ratio of from 10 to 40,000, depending on the amount of starting materials chosen, and can also be synthesized in an ether medium, for example in diethylene glycol dimethyl ether, in an alcoholic medium, such as methanol or 1,4-butanediol, or in water.

The borosilicate zeolites, including the isotactic borosilicate zeolites, can be synthesized, for example, at from 90° to 200° C. under autogenous pressure by reacting a boron compound, e.g. $H_3BO_3$, with a silicon compound, preferably finely divided silica, in aqueous amine solution, in particular in 1,6-hexanediamine or 1,3-propanediamine or triethylenetetramine solution, with or, in particular, without the addition of an alkali or alkaline earth. The borosilicate zeolites can also be prepared in ether solution, for example ethylene glycol dimethyl ether, or in alcoholic solution, for example 1,6-hexanediol, instead of in aqueous amine solution.

Ferrosilicate zeolites are obtained, for example, from an iron compound, preferably $Fe_2(SO_4)_3$, and a silicon compound, preferably finely divided silica, in aqueous amine solution, in particular 1,6-hexanediamine, with or without the addition of an alkali or alkaline earth, at from 100° to 220° C. under autogenous pressure.

The aluminosilicate, borosilicate and ferrosilicate zeolites thus prepared can be isolated, dried at from 100° to 160° C., preferably 110° C., and calcined at from 450° to 550° C., preferably from 500° to 540° C., and then molded with a binder in a weight ratio of from 90:10 to 40:60 to give extrudates or pellets. Suitable binders are various aluminas, preferably boehmite, amorphous aluminosilicates having an $SiO_2/Al_2O_3$ ratio of from 25:75 to 95:5, preferably 75:25, silica, preferably finely divided $SiO_2$, mixtures of finely divided $SiO_2$ and finely divided $Al_2O_3$, and clay. After the molding procedure, the extrudates or pellets are dried at 110° C. for 16 hours and calcined at 500° C. for 16 hours.

It is also possible for the isolated aluminosilicate or borosilicate zeolites to be molded directly after drying and not subjected to calcination until after the molding procedure. The aluminosilicate and borosilicate zeolites can be used in pure form, without a binder, as extrudates or pellets, the extrusion or peptizing assistants used being, for example, ethylcellulose, stearic acid, potato starch, formic acid, oxalic acid, acetic acid, nitric acid, ammonia, amines, esters of silicic acid and graphite or mixtures thereof.

If, because of its method of preparation, the zeolite is not in the catalytically active, acidic H form but, for example, in the Na form, the latter can be converted completely or partially into the desired H form by ion exchange, for example with ammonium ions, and subsequent calcination or by treatment with acids.

If, when the zeolite catalysts are used according to the invention, any deactivation occurs as a result of coking, it is advisable to regenerate the zeolites by burning off the coke deposit with air or with an air/$N_2$ mixture at from 400° to 550° C., preferably from 500° to 540° C. As a result, the zeolites regain their initial activity. By partial precoking, it is possible to adjust the activity of the catalyst to achieve optimum selectivity of the desired reaction product.

To achieve very high selectivity, high conversion and a long life, it is sometimes advantageous to modify the zeolites. A suitable method of modifying the catalysts is, for example, to dope the unmolded or molded zeolites with metal salts by ion exchange or by impregnation.

Advantageously, doping is carried out by a method in which the molded zeolites are initially taken in a riser tube and an aqueous or ammoniacal solution of a halide or of a nitrate of the metals is passed over at from 20° to 100° C. Ion exchange of this type can be carried out on the hydrogen, ammonium and alkali metal form of the zeolite. In another possible method for applying metal to zeolites, the zeolite material is impregnated, for example with a halide, a nitrate or an oxide of the metals in aqueous, alcoholic or ammoniacal solution. Both ion exchange and impregnation are followed by at least one drying step, or alternatively repeated calcination.

In another possible method of modification, the molded or unmolded zeolite material is treated with acids, such as hydrochloric acid, hydrofluoric acid and phosphoric acid, and/or steam.

The silicon-rich zeolites ($SiO_2/Al_2O_3 \geq 10$) which can be used include the known ZSM types as well as ferrierite and Nu-1 and Silicate ®, a molecular sieve, i.e. a silica polymorph.

Other catalysts for the preparation of benzyl ketones I from corresponding glycol monoethers II are described below: in particular, aluminum phosphates synthesized under hydrothermal conditions are used as aluminum phosphate catalysts for the novel process. The aluminum phosphates prepared under hydrothermal conditions are, for example, AlPO-5, AlPO-9, AlPO-11, AlPO-12, AlPO-14, AlPO-21, AlPO-25, AlPO-31 and AlPO-33. Syntheses for these compounds are described in EP-A-132 708, U.S. Pat. No. 4,310,440 and U.S. Pat. No. 4,473,663.

AlPO-5 can be synthesized, for example, by mixing orthophosphoric acid with pseudoboehmite (Catapal SB ®) in water, adding tetrapropylammonium hydroxide to this mixture and then carrying out the reaction at about 150° C. for from 20 to 60 hours under autogenous pressure in an autoclave. The AlPO-5 is filtered off, dried at from 100° to 160° C. and calcined at from 450° to 550° C. AlPO-9 can be synthesized from orthophosphoric acid and pseudoboehmite in aqueous DABCO solution (1,4-diazabicyclo[2.2.2]octane) at about 200° C. under autogenous pressure in the course of from 200 to 400 hours. AlPO-21 is synthesized from orthophosphoric acid and pseudoboehmite in aqueous pyrrolidone solution at from 150° to 200° C. under autogenous pressure in the course of from 50 to 200 hours.

The silicon aluminum phosphates used for the novel process are, for example, SAPO-5, SAPO-11, SAPO-31 and SAPO-34. The synthesis of these compounds is described in European Patent 103,117 and U.S. Pat. No. 4,440,871. These substances are obtained by crystallization from an aqueous mixture at from 100° to 250° C. under autogenous pressure in the course of from 2 hours to 2 weeks, the reaction mixture consisting of a silicon, aluminum and phosphorus component being reacted in an aqueous solution of an organic amine. SAPO-5, for example, is obtained by mixing $SiO_2$, suspended in aqueous tetrapropylammonium hydroxide solution, with an aqueous suspension of pseudoboehmite and orthophosphoric acid and then carrying out the reaction at from 150° to 200° C. in the course of 20 to 200 hours under autogenous pressure in a stirred autoclave. The powder is filtered off, dried at from 110° to 160° C. and calcined at from 450° to 550° C. Examples of other suitable silicon aluminum phosphates are ZYT-5, ZYT-6, ZYT-7, ZYT-9, ZYT-11 and ZYT-12 (JP 59/217-619).

Boron phosphates for the novel process can be prepared by mixing and kneading concentrated boric acid and phosphoric acid and by subsequent drying and calcination in an inert gas, air or steam atmosphere at from 250° to 650° C., preferably from 300° to 500° C. Examples of other suitable phosphates are $CePO_4$, $FePO_4$ and $Zr_3(PO_4)_4$. Silica and alumina can also be used as a catalyst.

The catalysts may alternatively be used in the form of 2–4 mm extrudates or as pellets having a diameter of 3 to 5 mm or as powders having particle sizes of from 0.1 to 0.5 mm or as a fluidizable catalyst.

The benzyl ketones I obtainable by the novel process are important intermediates for the preparation of amines or alcohols and for the synthesis of active ingredients and intermediates for scents.

Preparation of the catalysts

Catalyst A

An aluminosilicate zeolite of the pentasil type is prepared under hydrothermal conditions, under autogenous pressure and at 150° C., from 650 g of finely divided $SiO_2$ and 203 g of $Al_2(SO_4)_3 \cdot 18H_2$ in 10 kg of an aqueous 1,6-hexanediamine solution (weight ratio mixture 50:50) in a stirred autoclave. The crystalline reaction product is filtered off, washed thoroughly, dried at 110° C. for 24 hours and then calcined at 500° C. for 24 hours. The aluminosilicate zeolite contains 92.8% by weight of $SiO_2$ and 4.2% by weight of $Al_2O_3$.

Catalyst A is obtained by molding the pure aluminosilicate zeolite with a molding assistant to give 2 mm extrudates, which are dried at 110° C. for 16 hours and calcined at 500° C. for 24 hours.

Catalyst B

A borosilicate zeolite of the pentasil type is prepared in a hydrothermal synthesis from 640 g of finely divided $SiO_2$, 122 g of $H_3BO_3$ and 8 kg of an aqueous 1,6-hexanediamine solution (weight ratio mixture 50:50) at 170° C. under autogenous pressure in a stirred autoclave. The crystalline reaction product is filtered off, washed thoroughly, dried at 100° C. for 24 hours and then calcined at 500° C. for 24 hours. This borosilicate zeolite is composed of 94.2% by weight of $SiO_2$ and 2.3% by weight of $B_2O_3$.

This material is molded with a molding assistant to give 2 mm extrudates, which are dried at 110° C. for 16 hours and calcined at 500° C. for 24 hours.

EXAMPLES 1 TO 4

The reactions are carried out under isothermal conditions in a tube reactor (0.6 cm, 50 cm length) in the gas phase for not less than 6 hours. Separation and characterization of the reaction products are carried out by conventional methods. The quantitative determination of the reaction products and of the starting materials is effected by gas chromatography.

The experimental results are summarized in the table below.

TABLE

Starting material: 1-Methoxy-1-(3,4-methylenedioxy-phenyl)-propan-2-ol
Product: 1-Methoxy-1-(3,4-methylenedioxyphenyl)-propan-2-one

| | Example | | | |
|---|---|---|---|---|
| | 1 | 2 | 3 | 4 |
| Catalyst | A | A | B | B |
| Temperature [°C.] | 250 | 300 | 250 | 300 |
| WHSV [$h^{-1}$] | 1.9 | 2.1 | 1.8 | 2.2 |
| Conversion [%] | 99 | 99 | 99 | 99 |
| Selectivity End product [%] | 95.2 | 93.5 | 90.3 | 89.2 |

We claim:

1. A process for the preparation of a benzyl ketone of the formula

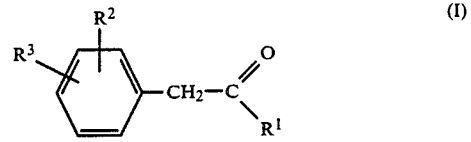

where $R^1$ is $C_1$–$C_8$-alkyl which is unsubstituted or substituted by cycloalkyl or aryl and $R^2$ and $R^3$ are each halogen, $C_1$–$C_4$-alkyl, hydroxyl, $C_1$–$C_4$-alkoxy or $C_2$–$C_4$-methylenedioxy, which comprises:
converting a glycol monoether of the formula

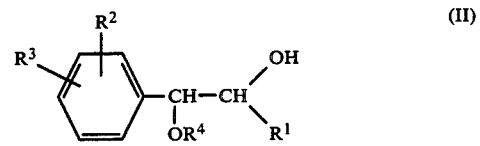

where $R^1$, $R^2$ and $R^3$ have the abovementioned meanings and $R^4$ is $C_1$–$C_8$-alkyl, into said benzyl ketone with elimination of the compound $R^4$—OH, in the presence of a catalyst selected from the group consisting of alumina, silica, phosphates and zeolites at from 50° to 500° C. and under from 0.01 to 50 bar.

2. A process as claimed in claim 1, wherein the catalyst used is an aluminosilicate, borosilicate, gallium silicate or ferrosilicate zeolite of the pentasil type.

3. A process as claimed in claim 1, wherein the phosphate used is aluminum phosphate, silicon aluminum phosphate, iron aluminum phosphate, iron silicon aluminum phosphate or boron phosphate.

4. A process as claimed in claim 1, wherein the catalyst used is silica.

5. A process as claimed in claim 1, wherein the reaction is carried out in the gas phase at from 100° to 500° C. and under from 0.01 to 50 bar.

6. A process as claimed in claim 1, wherein the phosphate used is an inorganic phosphate selected from the group consisting of $CePO_4$, $FePO_4$ and $Zr_3(PO_4)_4$.

* * * * *